（12) United States Patent
Vidu et al.

(10) Patent No.: US 11,779,465 B2
(45) Date of Patent: Oct. 10, 2023

(54) BIOCOMPATIBLE MEDICAL DEVICE AND METHOD OF MAKING SAME

(71) Applicants: Ruxandra Vidu, Citrus Heights, CA (US); Augustin Semenescu, Bucharest (RO); Ileana Mariana Mates, Bucharest (RO); Cristian Dragos Vidu, Citrus Heights, CA (US)

(72) Inventors: Ruxandra Vidu, Citrus Heights, CA (US); Augustin Semenescu, Bucharest (RO); Ileana Mariana Mates, Bucharest (RO); Cristian Dragos Vidu, Citrus Heights, CA (US)

(*) Notice: Subject to any disclaimer, the term of this patent is extended or adjusted under 35 U.S.C. 154(b) by 356 days.

(21) Appl. No.: 16/731,074

(22) Filed: Dec. 31, 2019

(65) Prior Publication Data

US 2021/0196465 A1 Jul. 1, 2021

(51) Int. Cl.
*A61F 2/28* (2006.01)
*A61F 2/00* (2006.01)
*A61F 2/30* (2006.01)

(52) U.S. Cl.
CPC .......... *A61F 2/2875* (2013.01); *A61F 2/0063* (2013.01); *A61F 2002/2835* (2013.01); *A61F 2002/30062* (2013.01); *A61F 2002/3084* (2013.01); *A61F 2002/30553* (2013.01); *A61F 2002/30599* (2013.01); *A61F 2310/00023* (2013.01)

(58) Field of Classification Search
CPC ................. A61F 2/2875; A61F 2/0063; A61F 2002/2835; A61F 2002/30062; A61F 2002/30553; A61F 2002/30599; A61F 2002/3084; A61F 2310/00023; A61F 2/30942; A61F 2002/2817; A61F 2002/30011; A61F 2002/3096; A61F 2250/0023; A61F 2250/0067; A61F 2210/0076; A61F 2/02; A61F 2/08; A61L 27/56; A61L 27/58
See application file for complete search history.

(56) References Cited

U.S. PATENT DOCUMENTS 9,433,438 B2 * 9/2016 Memmolo ........... A61B 17/688
10,420,861 B2 * 9/2019 Jeong .................. C12N 5/0654
(Continued)

*Primary Examiner* — Keri J Nelson
*Assistant Examiner* — Rebecca Lynee Zimmerman

(57) ABSTRACT

The present invention relates generally to biocompatible medical devices, such as cranial implants, and a method and means of attaching to bone. More specifically, the present invention relates to multilayered porous material with controlled porosity and drug load designed to control the release of drugs from a medical device. Additionally the present invention provides methods for controlling release of drugs by integrating the multilayer structure in medical devices with successive layers of polymer coatings of different porosities and drug contents. The multilayer material is inserted in between two plates such as meshes that provide strength to the implant. The present invention relates to biocompatible medical devices that has osseointegration and antibacterial properties. The present invention also relates to a method and means of attaching the medical device to defect in a bone structure and comprises of tree mounting parts configured to secure the medical in place.

15 Claims, 9 Drawing Sheets

(56) References Cited

U.S. PATENT DOCUMENTS

| | | | |
|---|---|---|---|
| 2005/0169893 A1* | 8/2005 | Koblish | A61L 27/56 |
| | | | 424/602 |
| 2005/0177118 A1* | 8/2005 | Hoganson | A61K 38/15 |
| | | | 623/1.42 |
| 2014/0081296 A1* | 3/2014 | Palmer | A61F 2/0063 |
| | | | 606/151 |
| 2014/0135852 A1* | 5/2014 | Memmolo | A61B 17/688 |
| | | | 606/324 |
| 2018/0078346 A1* | 3/2018 | Seo | A61L 31/06 |
| 2019/0201584 A1* | 7/2019 | Zhang | A61L 27/48 |
| 2021/0401564 A1* | 12/2021 | Neuenfeldt | A61L 27/3804 |

* cited by examiner

BIOCOMPATIBLE MEDICAL DEVICE AND METHOD OF MAKING SAME

BACKGROUND OF THE INVENTION

The surgical repair of a defect of the skull by cranioplasty has been practiced since ancient times, when materials of non-biological origin were used for this purpose. In the literature, there are data that attest that bone defects closed with silver plate or coconut bark were found in the collection of skulls of the Incas. In the etiological structure of acute brain lesions, brain trauma is in the first place, followed by vascular accidents (ischemic, hemorrhagic strokes), brain tumors, and diffuse post-resuscitation and post-strangulation cerebral hypoxia.

Traumatic brain injury is the leader in the ranking of mortality and invalidity. Of the total number of patients with severe head and intracranial injuries, more than 70% will remain with certain physical and mental disabilities. Also, it is recognized that every 11 minutes a child suffers from a head and brain trauma that causes significant disorders in their motor, linguistic and cognitive functioning throughout their life. In the literature, the disturbance of mnesic function is most often associated with intracranial trauma, which affects not only memory, but also other cognitive functions, such as learning. Intracranial traumas are the most common cause of death of people between the ages of 0 and 44 years old. Currently, about 11.5 million of Europe's population that survived from brain trauma suffers from certain forms of physical disabilities or mental impairment. There are approximately 500,000-600,000 cases of head injury in the US annually, of which more than 10% are fatal. While intracranial traumas have various mechanisms of occurrence, the most common causes are car accidents, aggression, trauma in sports and trauma by firearms. The trauma of the skull and brain is the most common type, more serious and in continuous ascension, of injury at childhood. There has been an increased incidence of severe head and brain trauma in children requiring surgical treatment.

The pathophysiological process secondary to a cranio-cerebral trauma is the occurrence and the propagation of cerebral edema, which results in increased intracranial pressure, decreased cerebral oxygenation and irreversible ischemic lesions that lead to permanent deficits and, in many cases, to death. Since the early 1970s, decompressive craniectomy is a neurosurgical method of combating refractory cerebral edema in drug therapy, due to the significant reduction of intracranial pressure and flow into the cerebral blood vessels. Although this aggressive way of lowering intracranial pressure has proven to be effective in saving the patient's life, severe deficiencies that may occur later have sparked controversy among neurosurgeons.

Like any surgical procedure, cranioplasty involves complications that may be related to the surgical technique and/or to the patient's tolerance to the plastic material used. It is known that a large variety of surgical techniques, materials and medical devices are used in performing cranioplasty procedures. With the evolution of the manufacturing systems, novel medical devices used in the reconstruction of the defects of the bone system have emerged in terms of the types of materials used and of the constructive forms, so that they are as close as possible to the anatomy of the patient.

Well-fitting prosthetic implants are required in large cranial defects to protect the patient's brain from trauma or infection, while it performs an aesthetic mission to restore the shape to the patient's head. Malleable and biocompatible materials are used to make an implant when not enough cranial bone is available for grafting. U.S. Pat. No. 7,747,305 presents a computer aided design method for producing an implant for a patient prior to operation using a non-invasive 3D (3-dimensional) scan of the patient's defect site that digitally represents the area that will receive the implant; designing and validating an implant on a computer based on digital data generated from a volume image of the patient; and fabricating the implant based solely on the implant design data generated on computer. Due to the advantages, the manufacture of personalized prostheses is currently considered the one that brings the most benefits in terms of compliance with the patient's needs. Also, a personalized prosthesis significantly reduces the duration of surgery and, implicitly, postoperative complications. However, an intracranial prosthesis that is custom made implies higher production costs compared to the standardized devices available on the market. However, drilling holes in skull is the main method used in cranioplasty to secure the cranial implant in place.

Other methods to secure in place the cranial implant have been sought. For example, U.S. Pat. No. 9,827,349 presents a composition as bone hemostat, bone adhesive, bone void filler, or bone cement. The surface of the plate has to be modified to ensure adherence. To obtain nanostructured surfaces, the prosthesis is modified by mechanical methods using abrasive materials, chemical methods using acid etching and electrochemical processes, physical methods or a combination of these methods. There are also other methods that involve different coatings on the surface of the implants. These coatings include hydroxyapatite, calcium phosphate biomimetic layers, biomolecule layers, but also coatings that have a combined synergistic effect. The main purpose of all these surface modification treatments is to improve the bioactivity, biocompatibility, wear resistance and corrosion of titanium and titanium alloys for their particular applications in medicine.

Surface modification of medical devices, such as cranial implants made of titanium mesh, can be applied to help induce the process of osseointegration. There are many clinical cases where the osseointegration process of Ti and its alloys is not enough but an osseo-inductive behavior of the implant surface is required, especially when rapid healing or bone quality and/or bone quantity is mandatory. One of the main objectives of the current research on biomaterials is the complex system of biological inducements and surface responses, including interface processes. Antibacterial surfaces capable of avoiding biofilm formation are extremely important for implants that are in direct contact with bone tissues. It was found that fewer macrophages and inflammatory reactions are reported on Ti and its alloy surfaces compared to stainless steel or polyether ketone surfaces. Titanium is well tolerated by the body, as long as the prosthesis is in perfect condition, mechanically stable and uninfected. If these conditions are not met, the prostheses may be associated with an acute or chronic inflammatory reaction, osteolysis, weakening and failure of the prosthesis. Therefore, the implant should have both osseointegration and antibacterial properties.

Human osteoclasts can corrode stainless steel, cobalt and Ti alloys, leading to the production of metal ions, which are toxic for the body and responsible for inflammatory reactions. The healing reaction in the case of a prosthesis made of Ti can occur by osseointegration, by fibrous encapsulation or by chronic inflammation. The last two reactions indicate the failure of the procedure. The events related to the inflammatory response of the body to the prosthesis is complex and include exudation, adsorption of the protein surface, development of a provisional blood-based matrix, recruitment of cells of the innate immune system (leukocytes, platelets), neutrophil migration, monocyte substitution and macrophage differentiation, foreign body reaction, production of reactive oxygen species, fusion of monocytes/macrophages to form giant cells or apoptosis.

Different strategies to obtain bioactive and antibacterial titanium surfaces have been investigated. The inorganic antibacterial agents that have been considered are mainly metal ions and nanoparticles, as well as their oxides (e.g. Ag, Cu, Zn and Ce). Among organic agents, mainly antibiotics have been considered.

The strategy to reduce the resistance to infections involves the modification of the biomaterial, that is, the modification of the design of the polymeric material following two main directions: 1) modification of the surface to minimize the adhesion of the bacteria; 2) incorporation of antimicrobial species with the role of destroying bacteria that contaminate the vicinity of the prosthesis (e.g. incorporation of antibiotics, silver, silver compounds etc).

The advantages of inorganic antibacterial agents are the broad spectrum of activities that allow the treatment of polymicrobial infections, the prevention of contamination with unknown bacteria and the development of resistance. Therefore, the problem of resistant bacterial strains is currently one of the most important problems regarding the use of antibiotics. However, the main disadvantages are their applications, which involve difficulties that come both from the field of bureaucracy, but especially with regard to finding the optimal therapeutic window, which will allow an effective antibacterial behavior, without cytotoxic effects.

The placement, fixation and fastening the implants to the bone structure are generally done by suturing or screwing the implant to the skull via holes. Drilling holes is the main method used in cranioplasty to repair a defect or deformity of the skull. Implant migration and micro-movements may hinder osseointegration and even result in rejection of the implant. Bone screws, tacks and the like are destructive intrusions into the bone structure and, once applied, exert (lateral) compressive forces on the bone structure. Compressive forces in turn may cause resorption of bone and loosening of the fixing means. Micro-movements due to play between different parts of the implant or the fixing means or between the fixing means and the bone structure and/or implant may increase damage and loosening and should be prevented. Further, the implant and its fixation means form an invasive volume inside the patient's body. Such volume should be minimal, in particular for a cranial implant to prevent damage to the brain.

BRIEF SUMMARY OF THE INVENTION

There remains a need in the art of biocompatible medical devices such as cranial implant system to be easily and efficiently inserted. The present invention describes a biocompatible medical device that include two supported meshes for providing mechanical strength and osseointegration properties of the implant, and a multiplayer porous material in between them that is loaded with the required bioactive antibacterial compound to promote a controlled and sustained release of the pharmaceutical agents at the site of surgical intervention. The composition gradient in the multilayer porous material is attained by loading successive layers of porous material with different amounts of bioactive materials and then stacking them to create a gradient of composition across the porous material.

The present invention describes method(s) to place, fix and fasten the medical device to the bone structure More particularly, the present invention relates to a method for accelerating the transport of the incorporated drug from the inner layers to the outer edge of the outer layer. The present invention describes a clamping system that provides a fast attachment of the biocompatible medical device to the bone structure and a rapid placement of the three layers of material with different properties. i.e. the two meshes that promote osseointegration of the implant and one multilayer porous material loaded with bioactive compounds having a gradient composition to control the release of the drugs incorporated in the porous material.

DETAILED DESCRIPTION OF THE INVENTION

The present invention is described more fully hereinafter with references to the accompanying drawings in which embodiments of the invention are shown. This invention may however be embodied in many different forms and should not be constructed as limited to the embodiments set forth herein. Rather these embodiments are provided so that this disclosure will convey the scope of the invention to those skilled in the art.

Figure 1A:
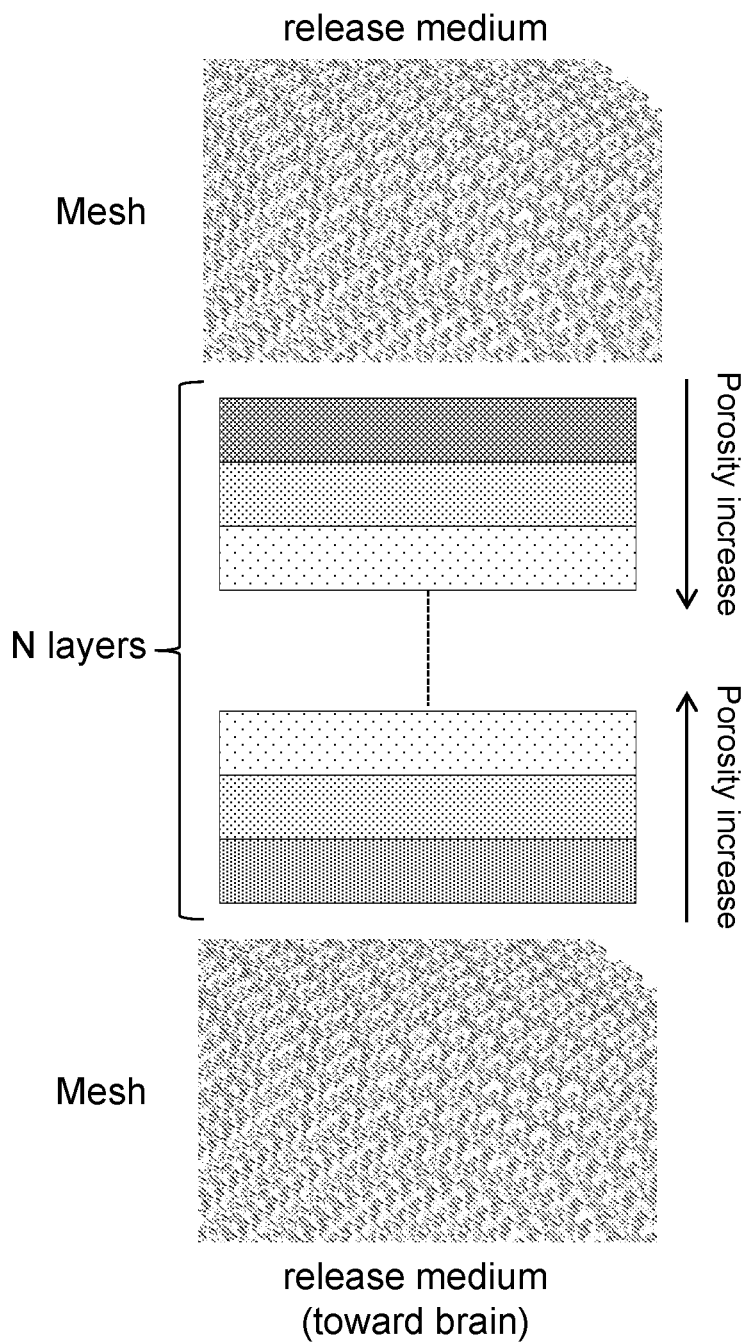
FIG. 1A is a drawing of the biocompatible medical device having in between 2 meshes a porous biomaterial comprising of successive layers of various porosities and dual gradient composition.
Figure 1B:
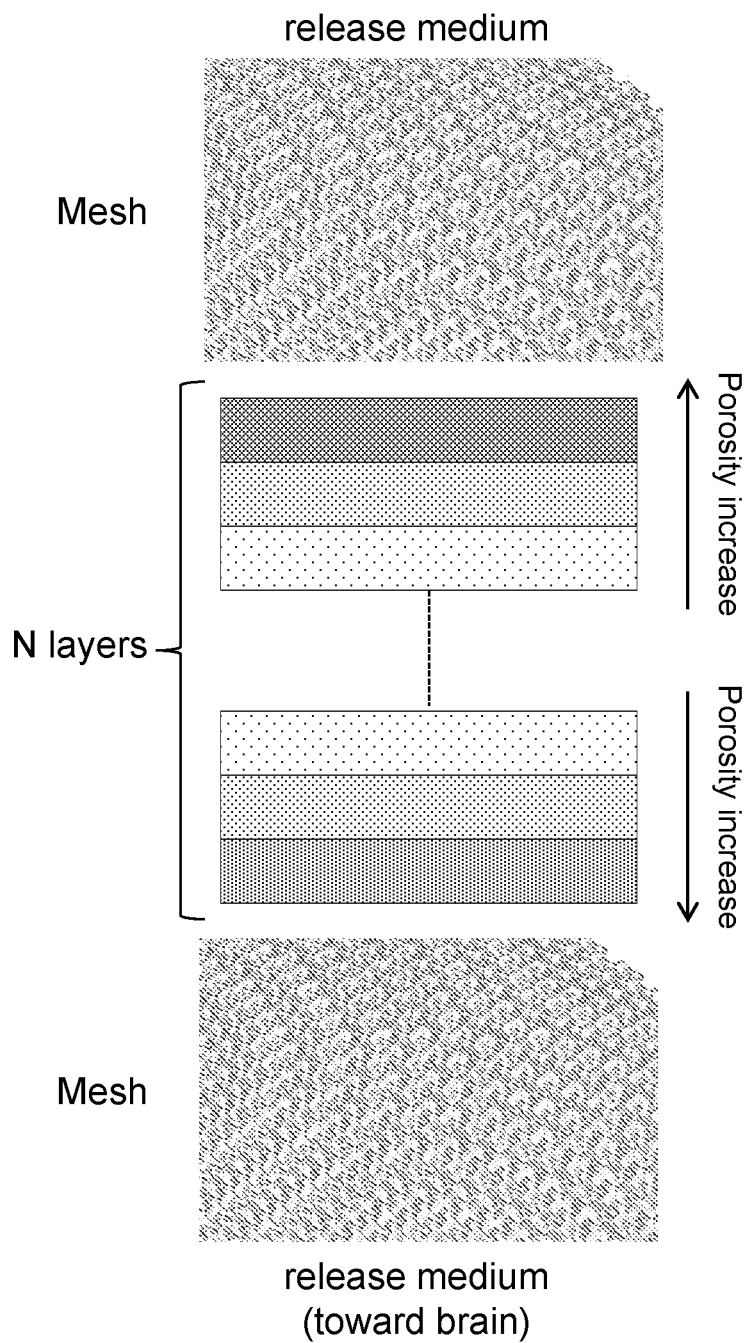
FIG. 1B is a drawing of the biocompatible medical device having in between 2 meshes a porous biomaterial comprising of successive layers of various porosities and dual gradient composition.
Figure 2:
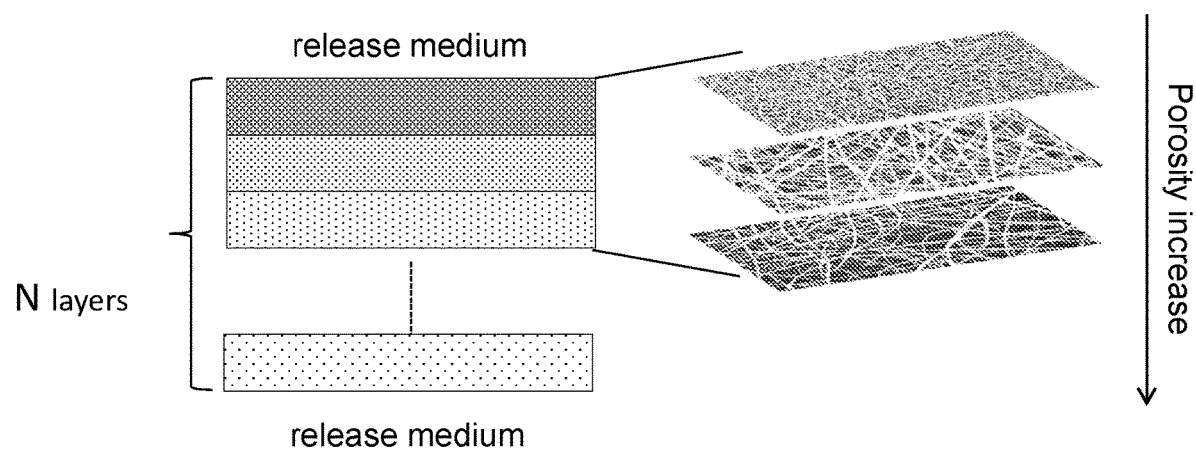
FIG. 2 is a drawing of the porous multilayer with simple gradient composition made of nanofibers.

With references to FIGS. 1-2 exemplary embodiments of the biocompatible medical devices that is configured according to the exemplary design of multilayer porous material integrated in between two structural meshes. The thickness of the multilayered assembly is equal or less the thickness of the skull.

In one embodiment, the intermediate layer is a porous membrane that includes a multitude of porous membranes that are formulated with the highest amount of bioactive material in the most porosity layer. Successive layers of polymeric nanofibers can be obtained by electrospinning. By varying the electrospinning variables conditions, various nanofibers sizes and porosities of the resulted membrane can be obtained. Nanofibers layer are obtained with progressive increased porosity.

The drug diffusion is the mechanism by which the drug is released in the body. In practice, blends consisting of a drug and polymer or blends of polymers are used. The morphology of the material and the molecular size of the drug are only a few factors that influence the diffusion of the drug into the body. The rate of releasing of a drug shows that a large amount of drug is discharged first, which indicates that the transport is nonlinear with a plateau. For the same drug, the rate of releasing is slowed down due to the resistance of polymer film.

The biocompatible medical device consist of a stuck of ultrathin membranes of various porosities, arranged in a double gradient of porosity as shown in FIG. 1A and FIG. 1B or simple gradient of porosity as shown in FIG. 2. FIG. 1A is a drawing of the biocompatible 185 medical device having in between 2 meshes a porous biomaterial comprising of successive layers of various porosities and stacked up from high to low porosity from the inside toward outside of the material. In FIG. 1B, successive layers of various porosities are stacked up from low to high porosity from the inside toward outside of the material.

Each membrane of a specific porosity is then loaded with bioactive agents, the amount of the drug being related to the amount of the drug retained by the membrane. Stacking up the membranes in a preset order controls the release the drug in a desired and precise fashion. The controlled release refers to the release of the pharmaceutic agents from the inside of a medical device to surface at a predetermined rate. The bioactive compound does not come off in an unpredictable fashion in a controlled release system, i.e. it does not discharge erratically in contact with a biological environment unless specifically intended to do so. Reducing the thickness of the layers, a continuous change in porosity can be obtained.

In some embodiments of the present invention an initial burst of drug may be desirable followed by a more gradual release thereafter. The release rate may be steady state (commonly referred to as "timed release" or zero-order kinetics), that is the drug is released in even amounts over a predetermined time (with or without an initial burst phase) or may be a gradient release A gradient release implies that the concentration of drug released from the device surface changes over time. The difference in porosity between adjacent layers can be used to control the release. In early stages of diffusion, the quantity of the bioactive compound delivered can be controlled by its distribution across the layers. Increasing the number of the layers with contrasting properties, the release profile can be engineered to better control the drug release. The effects of the relative thickness of the layers and the relative resistance to diffusion offered by each layer's composition on the drug release profile are critical. The dissimilarity in porosities of two adjacent layers can be used to control the release, while the quantity of drug delivered can be modified by varying the distribution of drug across the layers. Therefore, both microstructural and loading variances between multi-layers with porosity gradient can be used to tune the properties of the coating materials to obtain the desired drug release profile for a given application.

Electrospinning is a method of choice to produce fibers, which uses electric force to draw charged threads of polymer solutions or polymer melts up to fiber diameters in the order of nanometers. The process does not require coagulation or high temperatures to produce solid threads from solution. This makes the process particularly suited to the production of fibers using large and complex molecules. Electrospinning ensures that no solvent can be carried over into the final product. Depending on the size of the collector, large areas of membranes can be obtained. When a sufficiently high voltage is applied to a liquid droplet, the body of the liquid becomes charged, and electrostatic repulsion counteracts the surface tension and the droplet is stretched, at a critical point a stream of liquid erupts from the surface. This point of eruption is known as the Taylor cone. If the molecular cohesion of the liquid is sufficiently high, a charged liquid jet is formed. The size of an electrospun fiber can be in the nano scale and the fibers may possess nano scale surface texture, leading to different modes of interaction with other materials compared with macroscale materials. In addition to this, the ultra-fine fibers produced by electrospinning are expected to have two main properties, a very high surface to volume ratio, and a relatively defect free structure at the molecular level. This first property makes electrospun material suitable for activities requiring a high degree of physical contact, such as providing sites for chemical reactions, or the capture of small sized particulate material by physical entanglement—filtration. The second property should allow electrospun fibers to approach the theoretical maximum strength of the spun material, opening up the possibility of making high mechanical performance composite materials. Electrospinning have been used for medical purposes. The electrospun scaffolds made for tissue engineering applications can be penetrated with cells to treat or replace biological targets. Nanofibrous wound dressings have excellent capability to isolate the wound from microbial infections. Other medical textile materials such as sutures are also attainable via electrospinning. Through the addition of a drug substance into the electrospinning solution or melt diverse fibrous drug delivery systems and transdermal patches can be prepared.

In one embodiment of the present invention, the mesh has increased osseointegration properties and can be made of any titanium materials and compounds, synthetic resins, bone cements etc. To increase osseointegration, the mesh are designed with an open structure and coated with biocompatible materials such as hydroxyapatite. Surface modification of medical devices, such as cranial implants made of titanium mesh, can be applied to help induce the process of osseointegration. There are many clinical cases where the osseointegration process of Ti and its alloys is not enough but an osseo-inductive behavior of the implant surface is required, especially when rapid healing or bone quality and/or bone quantity is mandatory. Several strategies have been investigated; some of them are based on the bioactivity approach (i.e. hydroxyapatite precipitation induced "in vivo") and other are based on osteoblast stimulation through surface roughness. For Ti and its alloys, the bioactive behavior can be obtained by applying a layer of foreign material such as apatite or a bioactive glass using electrochemical processes such as anodic oxidation, or surface chemical treatments in acids or oxidative media. A classification of bioactive surfaces can be done according to the mechanism of bioactivity, which can be related to ion exchange process with the body fluids and/or with the effects of the topography of the surface of the prosthesis at micro and nano scale. Currently, the clinical demand has been oriented towards multifunctional surfaces, which are capable of simultaneously providing a specific response due to both colonization by different bone cells such as osteoblasts, fibroblasts, macrophages, and colonization with infectious agents such as bacteria and viruses.

In one embodiment of the present invention, polymethyl methacrylate (PMMA) can be reinforced with titanium mesh to increase its mechanical strength but also to increase the osteoconductive properties of the titanium mesh. PMMA is a synthetic resin produced from the polymerization of methyl methacrylate, was first used in medicine in the 1960s and is a polymerized organic combination of acrylic acid, transparent and easy to shape and. During the polymerization, the material solidifies in a short period of time, making it suitable for use in surgical procedures. The viscosity of the mixture increases rapidly, therefore the surgeon must model the cranial prosthesis in a very short time, which is why PMMA is suitable only for modeling small-sized cranial prostheses. In medical applications, however, we must take into account the chemical toxicity of the methyl methacrylate monomer but also the exothermic polymerization reaction to obtain PMMA. After polymerization, the low elasticity, but also the low resistance to mechanical stresses, makes PMMA susceptible to fracture under high mechanical pressure, which results in the production of particles by rubbing PMMA with a hard material surface. Thus, PMMA particles can provoke a cellular inflammatory response that can lead to osteolysis. This phenomenon is known as "cement disease". In order to improve the X-ray or CT examinations, zirconium dioxide can be added to PMMA. The most important advantages of PMMA are: transparency, ease of modeling, mechanical properties and low price. PMMA is well tolerated by the body so that immediately after implantation, fibrous tissue will develop at the interface between the material and surrounding tissue, and the osseointegration process will begin with a host reaction. The body's immune response is expressed both locally and systemically by activating macrophages.

In neurosurgery, PMMA is used in stabilizations and replacements of the vertebrae, but also in cranioplasty, either in the form of cement or in the form of solid pre-molded prosthesis. Thus, for small defects in the vertebrae or in the skull, the cement is prepared and molded intraoperatively, then fixed by the surgeon. For large skull defects, the preformed solid prosthesis should be very well sized and designed based on the patient's imaging results.

In addition, the use of PMMA cement is limited by the increase in temperature during polymerization, the toxicity of the liquid monomer and the reduction of vascularization at the interface between the material and surrounding tissue after implantation. In spine surgery, these factors can promote bone resorption, followed by failure of the procedure, while in cranial neurosurgery, increased temperature can affect surrounding tissues, causing even thermal necrosis of the healthy bone, thus affecting the nervous system. When PMMA is used in cranioplasty, the cranial prosthesis can be obtained by different methods such as modeled by hand during surgery, prefabricated or obtained intraoperatively using modern design methods. In the first case, the modeling of the cranial prosthesis by hand by the surgeon, intraoperatively, is a method used only in the case of very small size defects with relatively regular margins. In this case, no special tools are needed for cranial reconstruction. The surgeon models the prosthesis, then, after it is hardened, fixes it inside the cranial defect. The second situation is specific for larger head defects. In this situation, the prosthesis is performed before surgery, based on imaging investigations. Intraoperatively, the prefabricated prosthesis can be adjusted by the surgeon and then fixed by the patient's skull. The third situation involves the use of modern computer-aided design techniques, but also the use of a 3D printer. The prosthesis thus obtained is used as a mold for the prosthesis that the surgeon will model intraoperatively. After the material hardens and the prosthesis is to be implanted, holes are made at its periphery. The prosthesis is then placed inside the intracranial defect, and then fixed by the skull through suture threads. This technique is used especially for large skull defects with irregular edges. The prosthesis made in this way, by using the modern means of design and printing, will perfectly cover the cranial defect, the aesthetic result being clearly superior to the other two mentioned methods. The mesh made of titanium has been used as a support for PMMA placement, thus reducing the fracture potential of PMMA, especially in large-scale reconstructions of the skull cap. In addition, the base network may allow the intracranial prosthesis to be embellished when using PMMA.

Polymethyl methacrylate, is commonly known as bone cement, and is widely used for implant fixation in various orthopedic and trauma surgery. In reality, "cement" is a misnomer because, the word cement is used to describe a substance that bonds two things together. However, PMMA acts as a space-filler that creates a tight space which holds the implant against the bone and thus acts as a grout. Bone cements have no intrinsic adhesive properties, but they rely instead on close mechanical interlock between the irregular bone surface and the prosthesis. Other types of commercially available bone cement like calcium phosphate cements (CPCs) and Glass polyalkenoate (ionomer) cements (GPCs) are successfully used in a variety of orthopedic and dental applications. CPCs are bio resorbable and biocompatible, but are mainly used in cranial and maxillo-facial surgeries because of their low mechanical strength. Even though the uses and availability of various types of bone cement has greatly evolved over the past century, further research still continues to develop its more clinical applications and to reduce the adverse effects associated with their use.

In another embodiment of the present invention we can use hydroxyapatite (HA) to impregnate the titanium mesh, in order to increase the osteoconductive properties of the titanium mesh. Hydroxyapatite is a calcium phosphate stable in aqueous media, with the chemical formula $Ca_{10}(PO_4)_6(OH)_2$. HA contains approximately 40% calcium and 18.5% phosphorus (as a percentage by mass). The Ca/P ratio of hydroxyapatite is 1.667, which is an important indicator used to evaluate different processes for obtaining this material. It is known that about 70% of human bone is made from a non-stoichiometric form of hydroxyapatite, so that this material can be considered as an ideal bone replacement. Bone apatite contains the following elements: magnesium 0.7% wt, sodium 0.9% w; potassium 0.03% wt, chlorine 0.13% wt, fluorine 0.03% wt, trace elements: $Sr^{2+}$, $Pb^{2+}$, $Zn^{2+}$, $Cu^{2+}$, $Fe^{2+}$.

Hydroxyapatite has no cytotoxic or carcinogenic effect on the human body. It is characterized by high calcium content and high biocompatibility with regard to soft and hard tissues. For this reason, intracranial prostheses made of this type of ceramic material, can be used in direct contact with the bone. Also, the structure of synthetic hydroxyapatite may be similar to that of natural bones. By different manufacturing methods the size and number of pores can be controlled in the case of porous HA. The porous surface of the intracranial prosthesis can be covered by the new bone tissue that forms at the interface, which allows for a strong and lasting connection between the bone and the prosthesis. Currently, various forms of porous hydroxyapatite are available that are used either to repair bone defects or to support bone tissue regeneration in the human body. The solubility of HA is also a very important parameter, as these materials are designed to fill cavities or to be embedded in the surrounding bone tissue. This solubility depends on several factors such as i) the pH and solvent type (hydroxyapatite is insoluble in bases, but soluble in acids), ii) in potassium, sodium, magnesium and strontium salt solutions it dissolves better than in distilled water according to the following order Sr>Ba>Mg>Na>K, iii) the presence of amino acids, proteins, enzymes and other organic compounds. The solubility of HA under "in vivo" conditions is highly dependent on the degree of crystallinity, the size of the crystal, the amount of crystalline defects, stress level and porosity. Intracranial prostheses made from porous hydroxyapatite dissolve faster than densely structured prostheses due to the larger contact surface. Hydroxyapatite is manufactured and used in medicine both in dense and porous forms, as well as in granules and powders. The production process consists of several stages including obtaining powders, making prostheses, compaction and sintering, final treatment (sharpening the sharp edges), sterilization and packaging. In the process of manufacturing intracranial prostheses, antibiotics, growth factors and hormones or other cell types (drug delivery, cell cultures) may be introduced.

The realization of a pure phase of dense hydroxyapatite, with superior mechanical properties, is possible only by sintering powders with Ca/P in a molar ratio that correspond to the stoichiometric HA. Any differences in stoichiometry lead to the formation of tricalcium phosphate (TCP) and CaO as secondary phases. To obtain dense and porous HA, several methods may be used including sintering, cold isostatic pressing, injection molding, hot pressing and hot isostatic pressing. Ceramic materials such as hydroxyapatite, due to their biocompatibility, osteoinductivity and ability to create chemical bonds with living tissues, are considered as one of the most important materials used to make medical prostheses.

The dense hydroxyapatite materials cannot be absorbed, however, in the porous form, HA is biodegradable. Thus, the porous material is gradually replaced with regenerating bone, which makes the recovery process the same as implanting the autologous bone, where a simultaneous removal of the prosthesis by the osteoclasts and a new bone mineralization take place.

However, the HA geometry, the porosity and the substitution network remain the most important features involved in the healing process of bone defects. These properties have been tested on animals. In order to evaluate the biological properties of the non-stoichiometric form of hydroxyapatite, cell cultures were evaluated in terms of their chemical composition. Following the evaluation it was observed that hydroxyapatite with high carbonate content increased the activity of the osteoclasts, which suggests that bone resorption (the phenomenon underlined by the activity of the osteoclasts) is directly influenced by the functional groups incorporated in the crystalline hydroxyapatite network. Another conclusion relates to the substitutions of fluoride ions, which stimulate cell proliferation. However, there are some major disadvantages of hydroxyapatite, represented by its fragility that is specific ceramics, by the reduced resistance to stretching and by the high risk of infection after surgery. Larger bone defects can be difficult to repair with hydroxyapatite, due to the reduced osseointegration process and structural changes that occur in contact with the cerebrospinal fluid.

In another embodiment of the present invention the titanium mesh is impregnated with calcium phosphate. Calcium phosphate is the main component of human bone and has been used since the 1890s to stimulate bone regeneration. However, positive results were obtained only in 1920, when Albee discovered that tricalcium phosphate stimulates bone formation. In the 70's, it was discovered that the bioglass, i.e. glass containing calcium phosphate and hydroxyapatite ceramics, are osteoconductive. From that moment, calcium phosphate was widely used in medicine, in the research of novel medical prostheses and coatings.

The most used calcium phosphate ceramics include hydroxyapatite, tricalcium phosphate (TCP) and mixtures thereof (BCP—dicalcium phosphate). The dissolution behavior is the only important thing that differentiates them and implicitly the bioresorption rates. HA ceramics obtained from coral or synthetic apatite powder dissolve extremely slowly, compared to TCP ceramics which dissolve much faster. Although the TCP resorption rate is influenced to the same extent by both macrostructure and microstructure, TCP ceramics is considered a bioresorbable ceramic. These ceramics are characterized by a low mechanical strength, which is why their use in making prostheses is limited. However, they can be used to obtain cranial prostheses, but of small size. They are widely used as coatings for prostheses used in orthopedics but also for titanium nets used in cranioplasty. The metal matrix has the role of conferring the mechanical resistance necessary for the prosthesis, and the calcium phosphate comes with the osteoconductive properties that favor the process of osseointegration. HA, calcium phosphate cranioplasty prostheses are considered to have important regeneration and reintegration properties. For instance, Engstrand et al. (2015) has shown that an intracranial prosthesis made of calcium phosphate was manufactured by a casting technique, sterilized and then surgically implanted. After approximately 50 months after surgery, a revision of this prosthesis showed that the prosthesis was integrated and a vascularization network was developed. Also, the histological examination revealed a compact bone that was in direct contact with the remains of inert ceramic materials.

In another embodiment, natural polymeric film encapsulating propolis nano-formulation for cutaneous wound healing can be used. Cavalu et al. (2019) produced collagen films containing propolis encapsulated in chitosan nanoparticles, for biomedical applications such as cutaneous wound healing. The vibrational marker bands of propolis were well preserved in the final polymeric mixture, indicating the stability of bioactive compounds upon the encapsulation procedure. The antibacterial effect depends on the nanoparticles concentration in collagen film, the effect being more evident with respect to *E. coli* than *S. aureus*, while the antioxidant capacity indicated a synergic effect of chitosan nanoparticles matrix and propolis extract, incorporated in collagen films.

Figure 3:
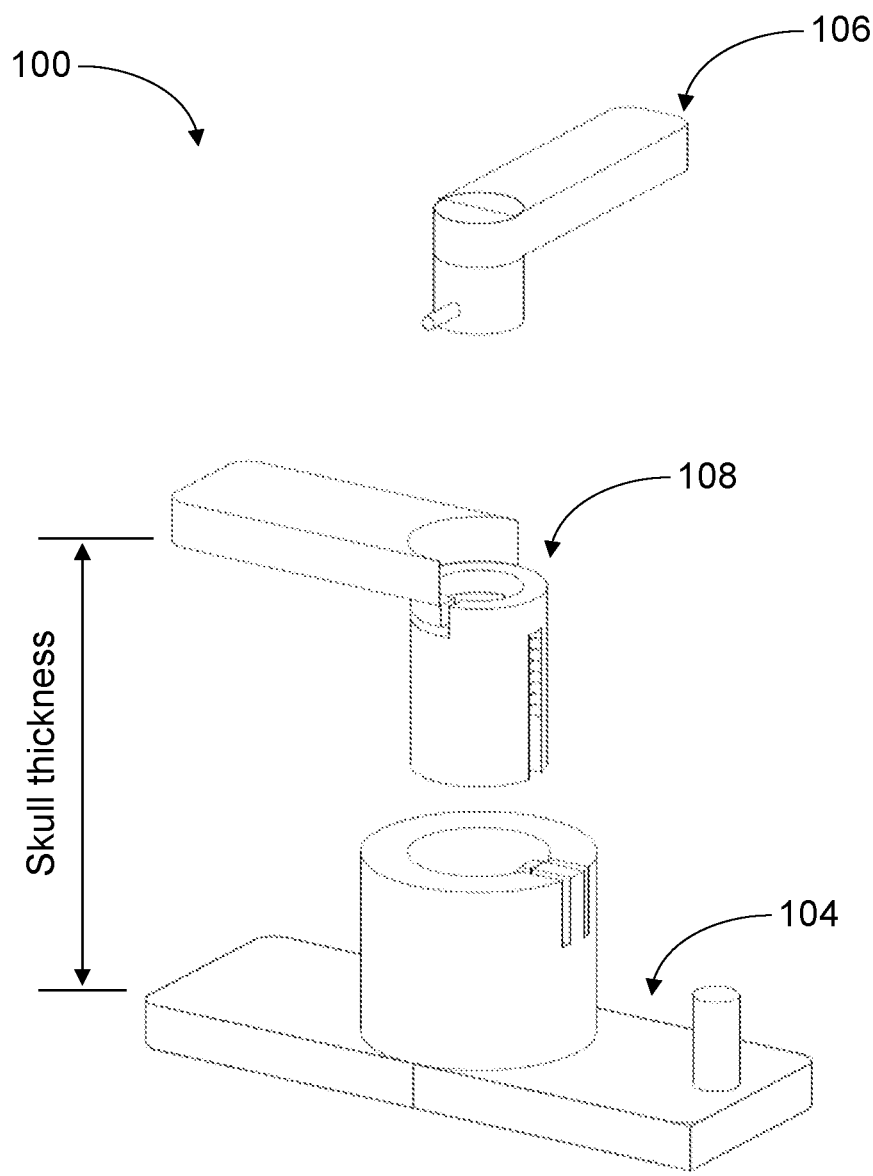
FIG. 3 is an illustration of the clamping system that can be used in cranioplasty containing 3 pieces that allow for placing and immobilizing the biocompatible medical device.

In another embodiment of the present invention, a clamping device that allows fixing the biocompatible medical device to the defect is presented in FIG. 3. The clamps further allows fixation such that the biocompatible medical device is placed and remains in position when the holding force between the fastener and the implant is reduced. The biocompatible device may not be custom made pre-operatively; instead the meshes and the multilayered porous material may be cut on the spot to fit the anatomic shape of the defect. The clamp-like mounting piece is pre-assembled at the extended position in a fast and secure way to the bone, while the actual assemble of the successive layers is hold in place by the fastening mechanism. The main function of this system is to fix the medical device to the bone structure, and to support and connect the meshes used in the implant for remodeling and restoring bone tissue such as cranial implants. Mashes may have a flat or a convex/concave surface to fit the original shape of the skull. As illustrated in FIG. 3, the clamping system 100 consists of three pieces: the lower piece 104, the upper piece 106 and the middle piece 108.

Figure 4:
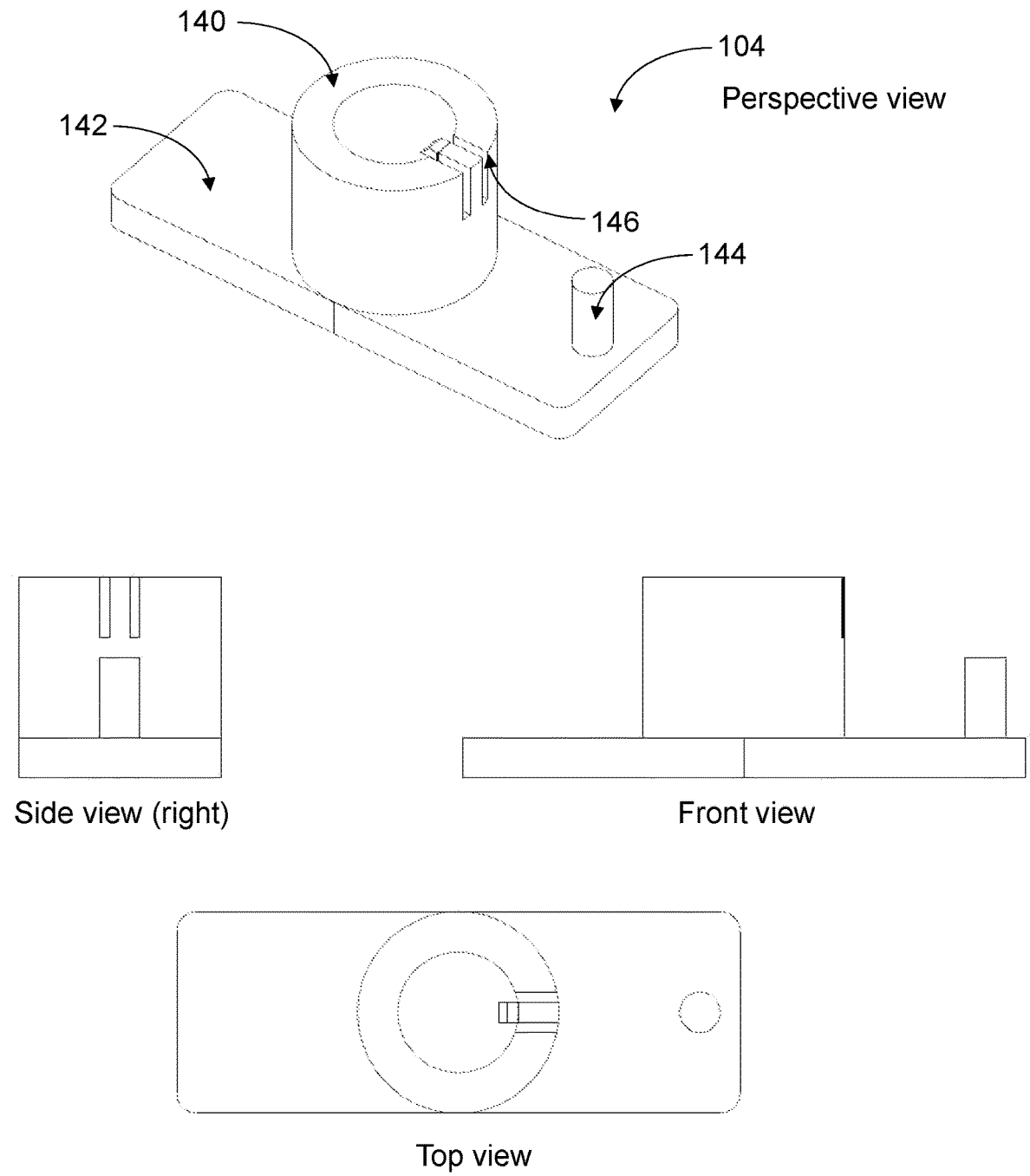
FIG. 4 is an illustration of various views of the lower piece of the clamping system.

FIG. 4 shows that the lower piece 104 has a cylindrical part 140 that sits on support 142. The cylindrical part 140 has a notch 146 that corresponds to the exterior groove 156 cut into the cylindrical part of the middle piece 108. The support 142 of the middle piece 108 has a knock on which the first mesh is placed.

Figure 5:
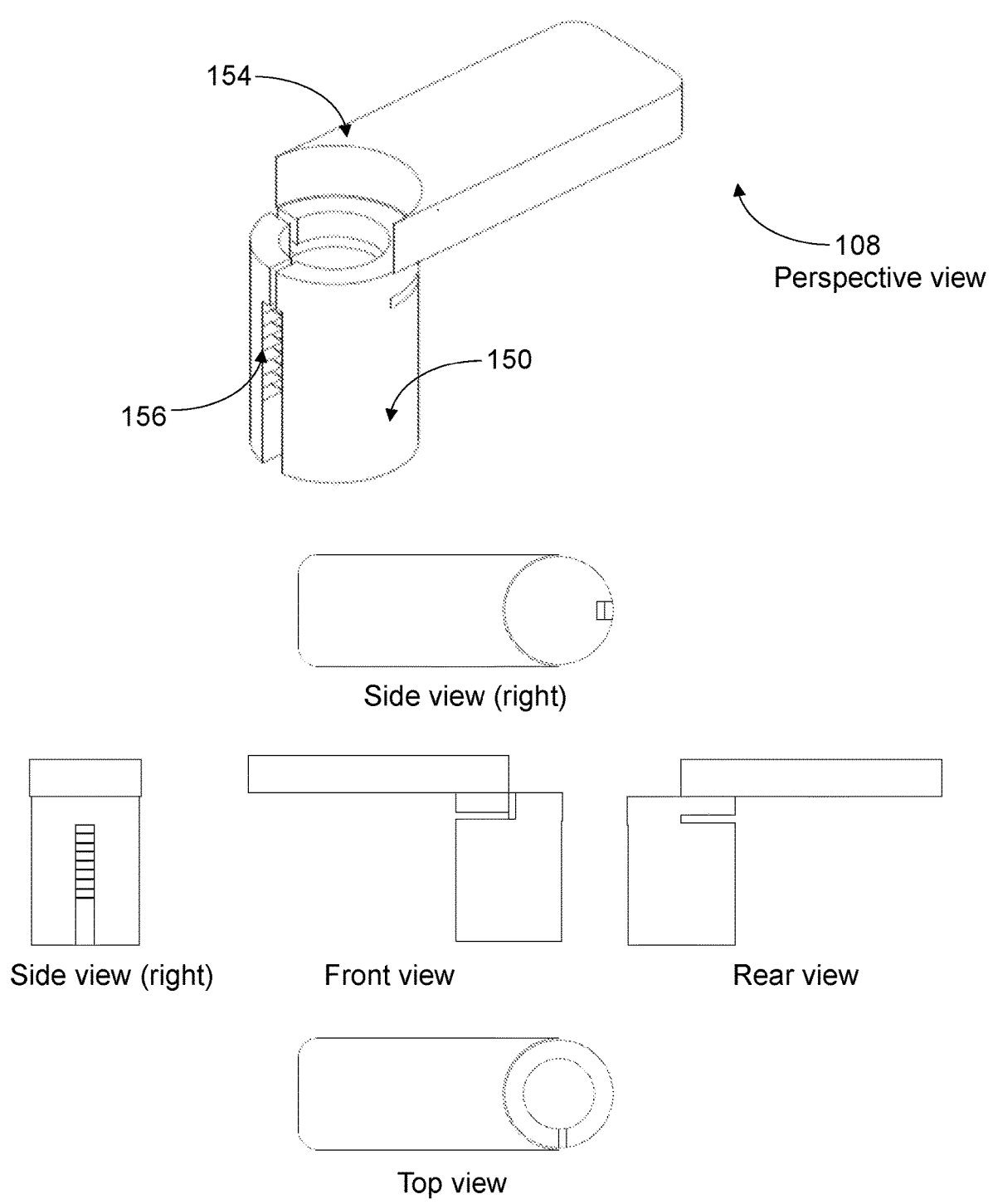
FIG. 5 is an illustration of various views of the middle piece of the clamping system.

FIG. 5 shows the middle piece 108 that helps adjust the height of the clamp to fit the thickness of the skull and supports the upper mesh. The middle piece 108 has an external groove on the cylinder 150 that helps adjust the height of the clamp. Part 154 is a bar that has the role to fasten the clamp to the bone structure.

Figure 6:
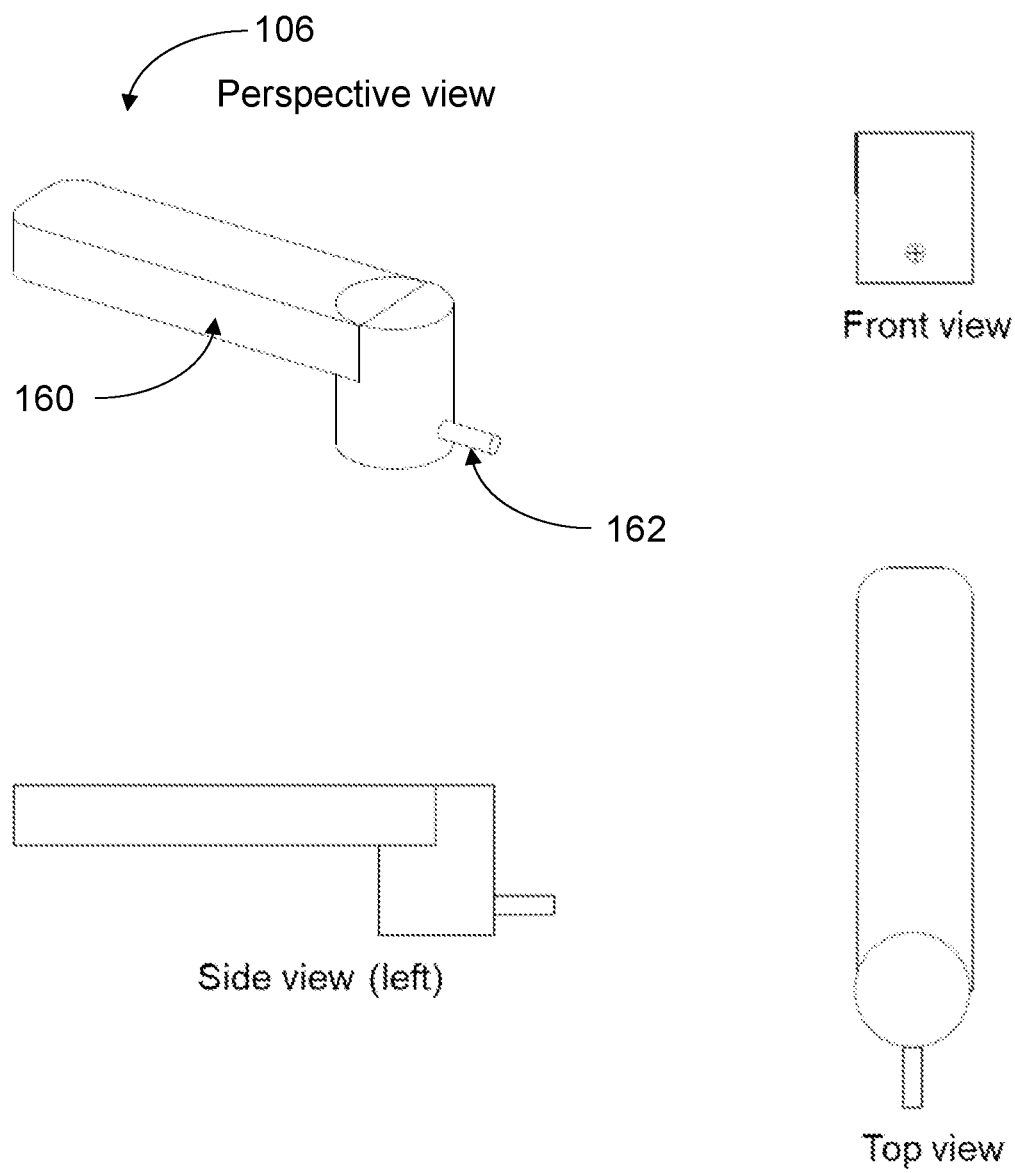
FIG. 6 is an illustration of various views of the upper piece of the clamping system.

FIG. 6 shows the upper part 106, which together fastens the clamp to the bone structure and to the biocompatible medical device. The upper part 106 has a lever 160 and a knob 162 that fix in place the clamp system. The upper lever 160 comes over the upper mesh when the level is rotated to a closed position.

In one embodiment, the attachment of the implant to the skull includes attaching the clamping system 100 to the edge of the cranial orifice at different points, creating a base for attaching the lower mesh. First, pieces 104 and 108 are pre-assembled at the maximum extension length, and then mounted at the edge of the skull and then tightened up until it is secured at the edge of the skull. This is possible because both part 104 and part 106 have a gear rack-like system that allows the two parts to be tightened up but do not allow them to move so that the assembly remains fixedly attached to the edge of the skull orifice. Then the first mesh is placed and hooked to the knock 144. The lower piece 104 has a hook 144 on the side of the support 142 that is oriented away from the skull, which has dual roles, i.e. to fasten the clamp to the skull and to attach the first mesh. After the lower mesh is placed, the multilayered porous material can be placed on the first mesh. This layer has anti-microbial properties with slow release of the drug. Then the top mesh is placed and the piece 104 is inserted and rotated to the ideal position for gripping and immobilizing the mesh.

Figure 7:
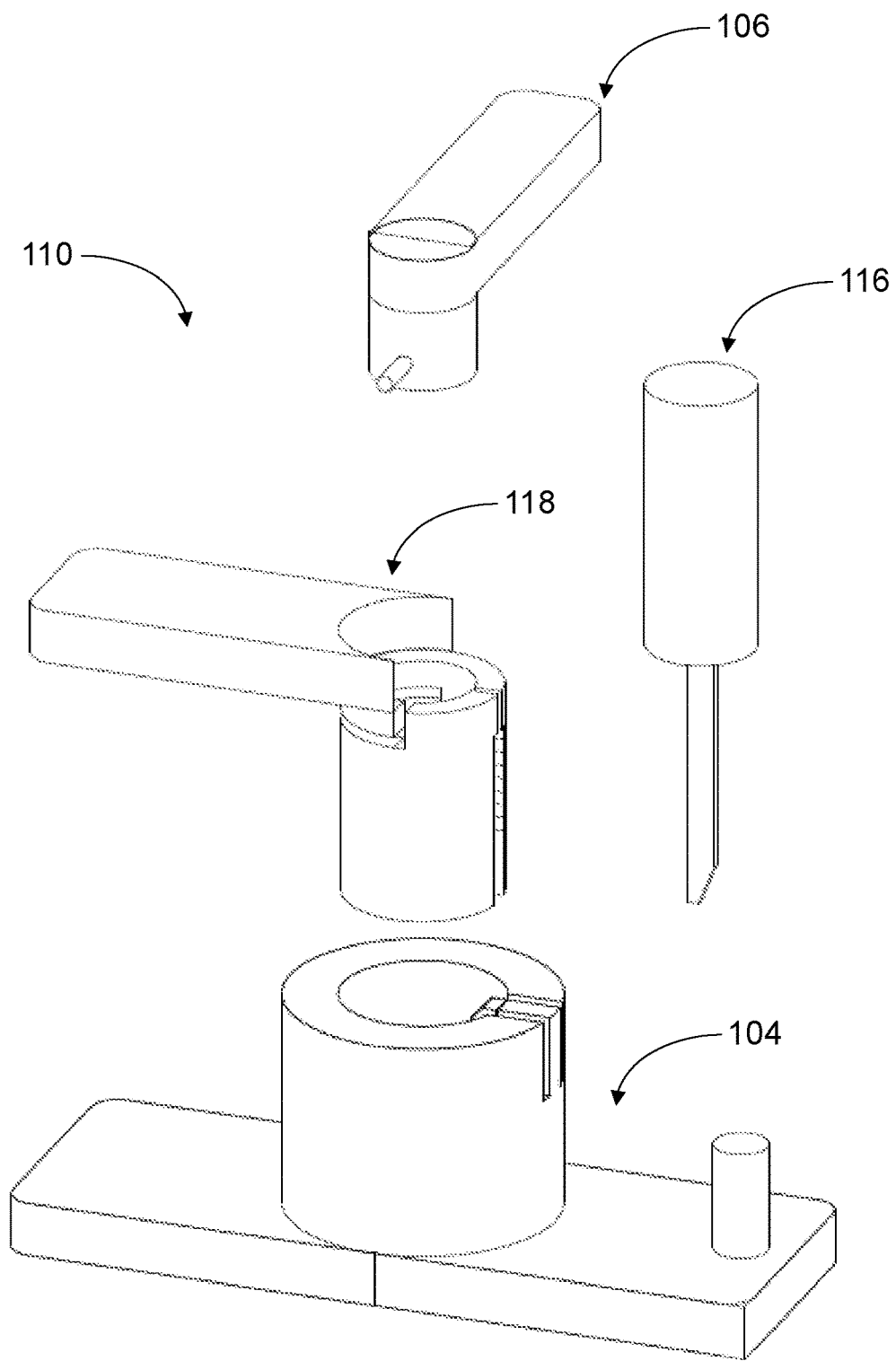
FIG. 7 is an illustration of the clamping system that can be used to fix an implant in a defect in the skull containing 3 pieces that allow for placing, immobilizing, and rearrangement of the implant.
Figure 8:
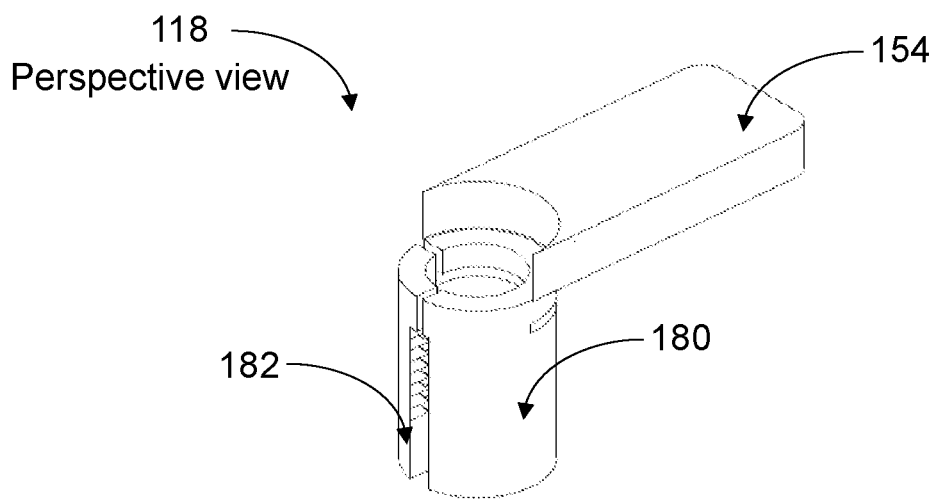
FIG. 8 is an illustration of various views of the middle piece 118 of the clamping system presented in FIG. 7.
Figure 8:
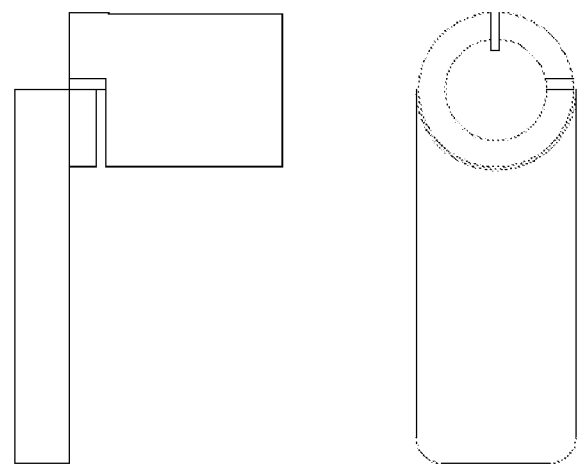
Figure 8:
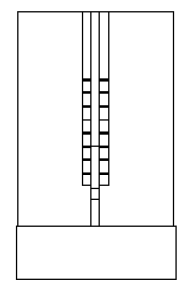

In some embodiments, the attachment of the implant is reversible such that the implant may be removed if complications, such as bleeding, occur. FIG. 7 shows a clamping system 110, which is similar to the clamping system 100, but the middle piece 118 differs from 108. The modification of middle pieces 118 is presented in details in FIG. 8, which shows that the external grove 182 is extended to the height of the cylinder 180 to allow for the insertion of key 116.

The proposed invention includes the following advantages: it decreases the surgical craniotomy time by simply pressing the clips and insert the plates; the two meshes doesn't have to be costumed made; the surgical procedure is more efficient due to the easiness of mounting operations including attaching the clips, laying the bottom mesh, laying the intermediate material, laying the upper mesh and fixing the upper mesh; the clamping system has a minimum height profile that helps to reduce the protrusions; the clamping system does not involve any invasive procedure for clamping the implant, such as drilling and screw clamps; easy placement of the gradient loaded multilayered porous material in between the meshes; a good contact interface of the upper mesh at the surface of the skull.

What is claimed is:

1. An implantable biocompatible medical device wherein the implant comprises two meshes having osseointegration properties and a porous material with controlled release properties that is placed in between the to meshes, wherein the porous material comprising multiple polymer layers of different porosities is loaded with drugs of different concentration, wherein the layers are arranged in a double gradient of porosity and stacked from high to low porosity from the inside toward outside of the porous material to control the release of drugs.

2. The assembly according to claim 1, wherein the implantable biocompatible medical device is a cranioplasty implant having a convex or concave shape.

3. The assembly according to claim 1, wherein the meshes are made of osteoconductive titanium materials and compounds resistant to hydrolysis to offer structural resistance and to promote osseointegration.

4. The assembly according to claim 1, wherein at least one of the two meshes has holes with diameters between 3000 and 10000 microns.

5. The assembly according to claim 1, wherein each layer of the multiple polymer layers can be made of biocompatible nanofibers.

6. The assembly according to claim 1, wherein said drug is selected from a group of antimicrobial compounds and loaded individually into each layer.

7. The assembly according to claim 1, wherein the meshes have curved surface.

8. The assembly according to claim 1 wherein said porous material comprises successive layers of various porosities and the successive layers are stacked from low to high porosity from one side of the porous material to the other side.

9. The assembly according to claim 1, wherein at least one of the two meshes is supported by a clamping system by a knock entering through at least one or more holes in at least one of the two meshes.

10. A clamping system comprising:
a lower piece including a support, and a cylindrical part and a knock sitting on the support, wherein the cylindrical part has a notch in a wall;
a middle piece including a cylindrical part and a bar connected to the cylindrical part of the middle piece, the cylindrical part of the middle piece having a groove in a top surface and a groove on an outside wall that correspond to the notch in the wall of the cylindrical part of the lower piece, wherein the bar is capable of rotating to fasten the clamp system to a skull;
an upper piece including a bar and a knob, the knob corresponding to the groove in the top surface of the cylindrical part of the middle piece, wherein the bar of the upper piece rotates to a closed position over an upper mesh; And
a key that can be used to rectify a position of an implant in a defect in the skull to allow placement, immobilization and rearrangement of the implant.

11. The clamping system according to claim 10, wherein the support of the lower piece attaches to an inner part of the skull surface and supports an inner mesh.

12. The clamping system according to claim 10, wherein the bar of the middle piece attaches to an external surface of the skull and fastens the pre-assembled clamp at the edge of the skull.

13. The clamping system according to claim 10, wherein the key can be used to rearrange the clamping system should readjustments be required.

14. A method for attaching an implantable medical device to a skull, comprising:
- pre-assembling lower and middle pieces of a clamping system at an extended position required to accommodate a thickness of the skull;
- positioning the pre-assembled lower and middle pieces of the clamping system to an edge of the skull, sliding toward the skull, and fixing it in place with a gear-like part of the middle piece, and rotating a bar on top of the middle piece to fasten the pre-assembled lower and middle pieces of the clamping system to the skull;
- placing a first mesh on the lower piece of the clamping system and hooking it to a knock;
- placing a porous biomaterial comprising successive layers on top of the first mesh;
- placing a second mesh above the porous biomaterial comprising successive layers;
- positioning an upper piece of the clamping system on top of the pre-assembled lower and middle pieces and inserting it into the middle piece while aligning a knob of the upper piece with a groove in a top surface of a cylinder of the middle piece to lock its position; and
- rotating a bar of the upper piece to secure and immobilize the implantable medical device.

15. The method of claim 14, wherein a plurality of clamp systems can be used to hold in place the implantable medical device.

\* \* \* \* \*